United States Patent
Usami

(10) Patent No.: US 9,439,554 B2
(45) Date of Patent: Sep. 13, 2016

(54) ENDOSCOPE HAVING CONNECTOR PART WITH OUTPUT SELECTOR

(71) Applicant: OLYMPUS CORPORATION, Tokyo (JP)

(72) Inventor: Hiroyuki Usami, Nishitokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/883,194

(22) Filed: Oct. 14, 2015

(65) Prior Publication Data

US 2016/0029874 A1 Feb. 4, 2016

Related U.S. Application Data

(63) Continuation of application No. PCT/JP2014/059735, filed on Apr. 2, 2014.

(30) Foreign Application Priority Data

Apr. 19, 2013 (JP) ................. 2013-088328

(51) Int. Cl.
*A61B 1/05* (2006.01)
*A61B 1/00* (2006.01)
(Continued)

(52) U.S. Cl.
CPC ....... *A61B 1/00013* (2013.01); *A61B 1/00004* (2013.01); *A61B 1/00009* (2013.01);
(Continued)

(58) Field of Classification Search
CPC .......... A61B 1/00013; A61B 1/00009; A61B 1/00006; A61B 1/05; A61B 1/00114; A61B 1/00124; A61B 1/00126; G02B 23/2484
See application file for complete search history.

(56) References Cited

U.S. PATENT DOCUMENTS

| 4,983,019 A | 1/1991 | Ikuno et al. |
| 2006/0287576 A1* | 12/2006 | Tsuji ................. A61B 1/00105 600/132 |

(Continued)

FOREIGN PATENT DOCUMENTS

| JP | S63-146813 U | 9/1988 |
| JP | S63-274905 A | 11/1988 |

(Continued)

OTHER PUBLICATIONS

International Search Report dated Jul. 8, 2014 issued in PCT/JP2014/059735.

(Continued)

*Primary Examiner* — John P Leubecker
(74) *Attorney, Agent, or Firm* — Scully, Scott, Murphy & Presser, PC

(57) ABSTRACT

An endoscope which is configured to be connected to an external processing device includes: an insertion part; a distal end part including an imaging unit configured to generate image information and an E/O converter configured to convert the image information into an optical signal and to output the converted optical signal; a connector part including an O/E converter configured to convert the optical signal into an electric signal, a first output unit configured to convert the electric signal into serial data and to output the converted serial data to the processing device, a second output unit configured to convert the electric signal into an optical signal and to output the converted optical signal to the processing device, and a selector configured to select one of the first output unit and the second output unit; and an optical fiber connecting the E/O converter to the O/E converter.

1 Claim, 6 Drawing Sheets

(51) Int. Cl.
 *A61B 1/045* (2006.01)
 *G02B 23/24* (2006.01)
 *A61B 1/04* (2006.01)
 *H04N 7/18* (2006.01)

(52) U.S. Cl.
 CPC ............. *A61B1/00117* (2013.01); *A61B 1/04* (2013.01); *A61B 1/045* (2013.01); *G02B 23/2484* (2013.01); *A61B 1/00124* (2013.01); *A61B 1/00126* (2013.01); *A61B 1/05* (2013.01); *H04N 7/18* (2013.01)

(56) References Cited

U.S. PATENT DOCUMENTS

| | | |
|---|---|---|
| 2008/0039686 A1 | 2/2008 | Mori et al. |
| 2008/0143827 A1 | 6/2008 | Yoshizumi et al. |
| 2013/0012777 A1* | 1/2013 | Baum ................ A61B 1/00013 600/110 |
| 2013/0096380 A1 | 4/2013 | Matsuzawa et al. |
| 2013/0235175 A1* | 9/2013 | Kazama .................. H04N 7/18 348/65 |
| 2014/0320619 A1* | 10/2014 | Nakamura ......... A61B 1/00036 348/65 |

FOREIGN PATENT DOCUMENTS

| | | |
|---|---|---|
| JP | 2001-028709 A | 1/2001 |
| JP | 2006-055350 A | 3/2006 |
| JP | 2008-036356 A | 2/2008 |
| JP | 2008-149027 A | 7/2008 |
| JP | 2009-056240 A | 3/2009 |
| JP | 5155496 B2 | 3/2013 |
| WO | WO 2012/046856 A1 | 4/2012 |

OTHER PUBLICATIONS

Japanese Office Action dated Feb. 3, 2015 issued in JP 2014-553575.

Japanese Office Action dated Jun. 3, 2015 issued in JP 2014-553575.

* cited by examiner

ENDOSCOPE HAVING CONNECTOR PART WITH OUTPUT SELECTOR

CROSS-REFERENCE TO RELATED APPLICATIONS

This application is a continuation of PCT international application Ser. No. PCT/JP2014/059735 filed on Apr. 2, 2014 which designates the United States, incorporated herein by reference, and which claims the benefit of priority from Japanese Patent Application No. 2013-088328, filed on Apr. 19, 2013, incorporated herein by reference.

BACKGROUND

1. Technical Field

The disclosure relates to an endoscope including an imaging element capable of outputting, as image information, a photoelectrically-converted electric signal from a pixel arbitrarily designated to be read among a plurality of pixels for imaging and also relates to a processing device for performing predetermined image processing with respect to the image information transmitted from the imaging device.

2. Related Art

Conventionally, in a medical field, an endoscope system has been used to observe an organ of a subject such as a patient. The endoscope system has, for example, a flexible elongated shape and includes an imaging device (electronic scope) inserted into a body cavity of a subject, an imaging element which is provided at a distal end of the imaging device and which captures an in-vivo image, a processing device (external processor) which performs predetermined image processing with respect to the in-vivo image captured by the imaging element, and a display device capable of displaying the in-vivo image on which the image processing is performed by the processing device. In a case of acquiring an in-vivo image by using the endoscope system, an insertion part is inserted into the body cavity of the subject and illumination light is emitted from the distal end of the insertion part to a body tissue in the body cavity. Then, the imaging unit captures the in-vivo image. A user such as a doctor observes an organ of the subject based on the in-vivo image displayed on the display device.

As such an endoscope system, a technology to output in-vivo image information, which is captured by an imaging element, as an optical signal to a processing device has been known (see Japanese Laid-open Patent Publication No. 2008-36356). In this technology, it is possible to reduce the number of transmission lines which connect the imaging device to the processing device. Thus, it is possible to reduce a diameter of an insertion part.

SUMMARY

In some embodiments, an endoscope which is configured to be connected to an external processing device and to transmit and receive information to and from the processing device includes: an insertion part configured to be inserted into a body cavity of a subject; a distal end part provided at a distal end of the insertion, the distal end part including an imaging unit configured to generate image information and an E/O converter configured to convert the image information generated by the imaging unit into an optical signal and to output the converted optical signal; a connector part connected to the processing device, the connector part including an O/E converter configured to convert the optical signal output from the E/O converter into an electric signal, a first output unit configured to convert the electric signal converted by the O/E converter into serial data and to output the converted serial data to the processing device, a second output unit configured to convert the electric signal converted by the O/E converter into an optical signal and to output the converted optical signal to the processing device, and a selector configured to select, based on identification information of the processing device, one of the first output unit and the second output unit as an output unit to output the image information; and an optical fiber connecting the E/O converter to the O/E converter.

The above and other features, advantages and technical and industrial significance of this invention will be better understood by reading the following detailed description of presently preferred embodiments of the invention, when considered in connection with the accompanying drawings.

DETAILED DESCRIPTION

In the following, as a mode to carry out the present invention (hereinafter, referred to as "embodiment"), a medical endoscope system to shoot and display an image in a body cavity of a subject such as a patient will be described. Also, the present invention is not limited to the embodiment. Also, the same reference signs are used to designate the same parts throughout the drawings. Moreover, the drawings are schematic. A relationship between a thickness and a width of each part, a proportion of each part, and the like are different from the reality. Also, the drawings may include parts with sizes or proportions different from each other.

First Embodiment

Figure 1:
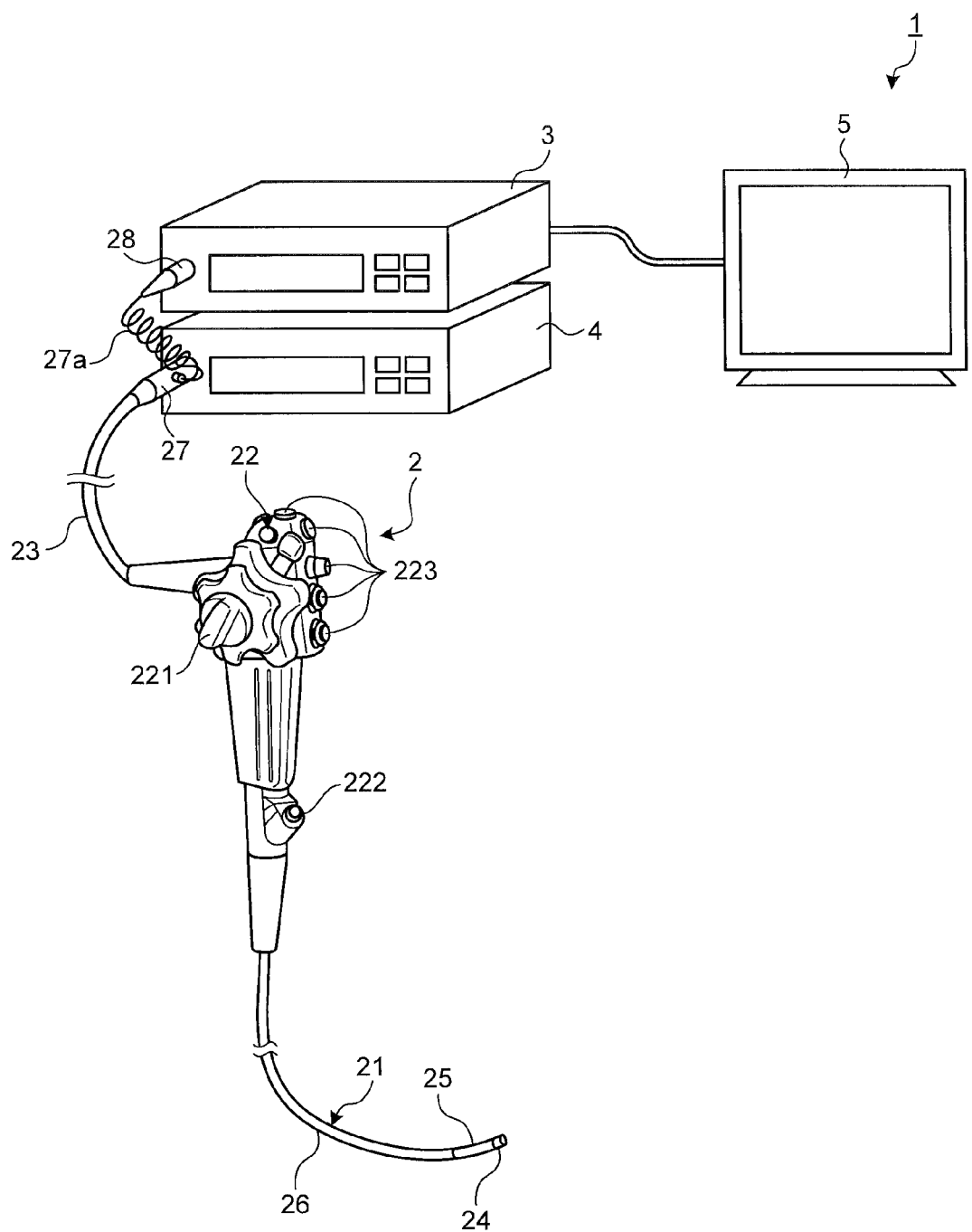
FIG. 1 is a view illustrating a schematic configuration of an endoscope system according to a first embodiment of the present invention.
Figure 2:
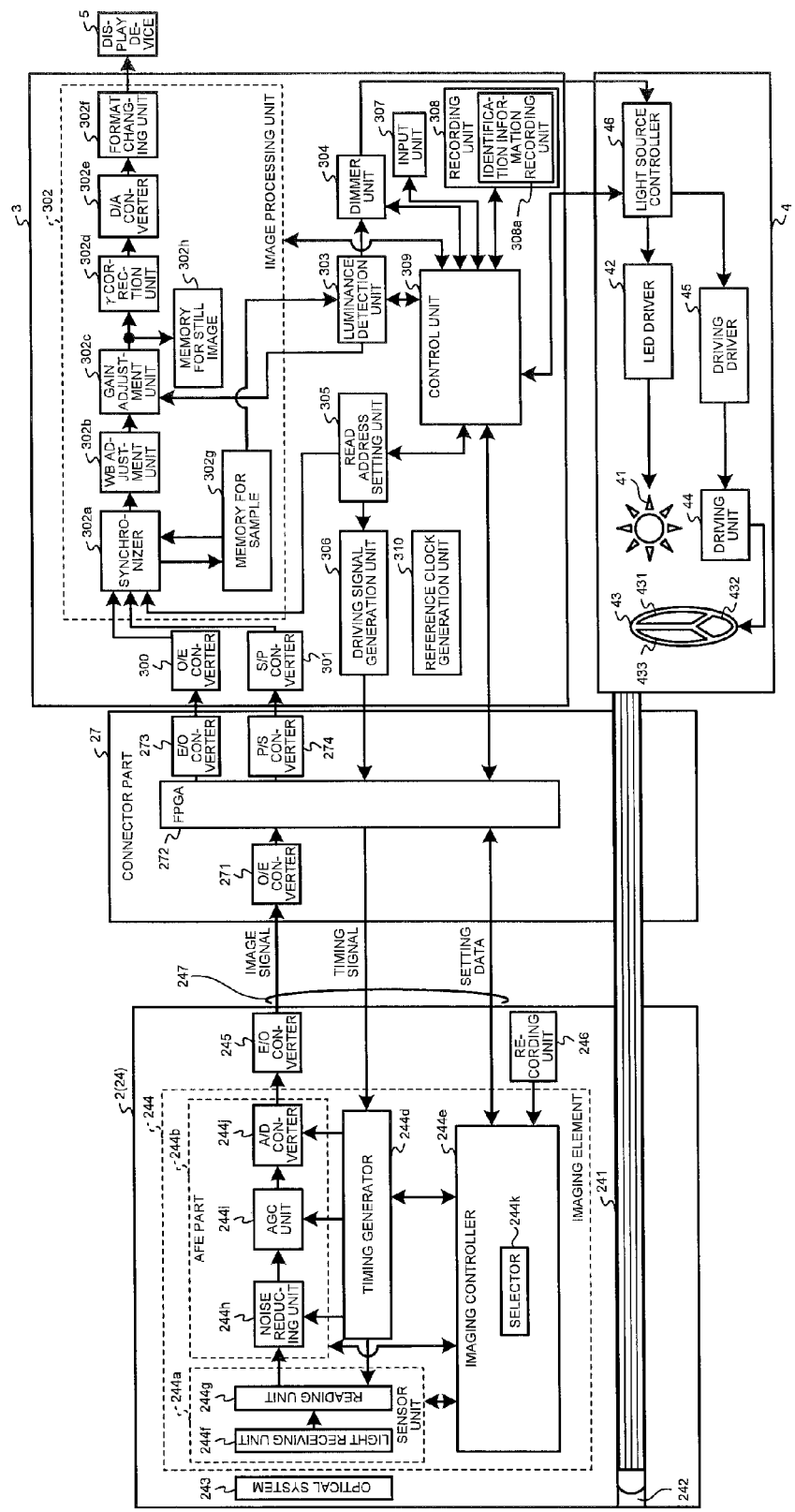
FIG. 2 is a block diagram illustrating a functional configuration of a main part of the endoscope system according to the first embodiment of the present invention.

FIG. 1 is a view illustrating a schematic configuration of an endoscope system according to the first embodiment of the present invention. FIG. 2 is a block diagram illustrating a functional configuration of a main part of the endoscope system according to the first embodiment of the present invention. As illustrated in FIG. 1 and FIG. 2, an endoscope system 1 includes an endoscope 2 (electronic scope) which functions as an imaging device to capture an in-vivo image of a subject by insertion of a distal end part into a body cavity of a subject, a processing device 3 (external processor) which performs predetermined image processing with respect to the in-vivo image captured by the imaging device and which totally controls an operation of the whole endoscope system 1, a light source device 4 which generates illumination light emitted from a distal end of the endoscope 2, and a display device 5 which displays the in-vivo image on which the image processing is performed by the processing device 3.

The endoscope 2 includes a flexible insertion part 21 having an elongated shape, an operating unit 22 which is connected to a proximal end side of the insertion part 21 and which receives an input of various operation signals, and a universal cord 23 which is extended in an opposite direction of a direction, in which the insertion part 21 is extended from the operating unit 22, and which includes various cables for connecting the processing device 3 to the light source device 4.

The insertion part 21 includes a distal end part 24 including an imaging element described later, a bend part 25 which includes a plurality of bend pieces and which can be bended, and a long flexible tube part 26 which is connected to a proximal end side of the bend part 25 and which has flexibility.

The distal end part 24 includes a light guide 241 which includes a glass fiber or the like and which forms a guiding path of the light emitted from the light source device 4, an illumination lens 242 provided at a distal end of the light guide 241, an optical system 243 to collect light, an imaging element 244 which is provided at an image-formed position of the optical system 243 and which receives the light collected by the optical system 243, photoelectrically converts the light into an electric signal, and performs predetermined signal processing, an E/O converter 245 which converts the electric signal input from the imaging element 244 into an optical signal, and a recording unit 246 which records various kinds of information of the endoscope 2.

The optical system 243 includes one or a plurality of lenses and has an optical zoom function to change an angle of view and a focus function to change a focal point.

The imaging element 244 includes a sensor unit 244a which photoelectrically converts the light from the optical system 243 to output an electric signal, an analog front end 244b (hereinafter, referred to as "AFE part 244b") to perform noise rejection or A/D conversion with respect to the electric signal output from the sensor unit 244a, a timing generator 244d to generate driving timing of the sensor unit 244a and a pulse of various kinds of signal processing in the AFE part 244b, and an imaging controller 244e to control an operation of the imaging element 244. The imaging element 244 is a complementary metal oxide semiconductor (CMOS) image sensor.

The sensor unit 244a includes a light receiving unit 244f in which a plurality of pixels each of which includes a photodiode to accumulate a charge corresponding to a light quantity and an amplifier to amplify the charge accumulated by the photodiode is arranged two-dimensionally in a matrix, and a reading unit 244g to read, as image information, an electric signal generated by a pixel which is arbitrarily set to be read among the plurality of pixels in the light receiving unit 244f.

The AFE part 244b includes a noise reducing unit 244h to reduce a noise component included in an (analog) electric signal, an auto gain control (AGC) unit 244i which adjusts an amplification factor (gain) of the electric signal to keep a constant output level, and an A/D converter 244j to perform A/D conversion of the electric signal output through the AGC unit 244i. The noise reducing unit 244h reduces a noise by using a correlated double sampling method.

The imaging controller 244e controls various operations of the distal end part 24 according to setting data received from the processing device 3. The imaging controller 244e includes, for example, a central processing unit (CPU). The imaging controller 244e includes a selector 244k.

Based on the setting data received from the processing device 3, the selector 244k selects one of a first output unit and a second output unit as an output unit to output image information (image signal) generated by the imaging element 244. For example, based on the setting data received from the processing device 3, the selector 244k selects a transmission line of the image information generated by the imaging element 244. More specifically, based on the identification information of the processing device 3 which information is received from the processing device 3, the selector 244k selects one of an electric signal and an optical signal as a signal output from a connector part 27 described later. Here, the identification information includes, for example, ID information for identification of a model of the processing device 3, transmission information capable of corresponding to an electric signal or an optical signal, and an observation method of the light source device 4.

The E/O converter 245 converts the electric signal output from the imaging element 244 into an optical signal and outputs the converted signal to the connector part 27 described later. Note that a cable for connecting the imaging element 244 to the connector part 27 includes an optical fiber or the like.

The recording unit 246 records various kinds of information of the endoscope 2. More specifically, the recording unit 246 records identification information to identify the endoscope 2, type information or individual information of the imaging element 244, and various programs executed by the imaging controller 244e.

The operating unit 22 includes a bend knob 221 to bend the bend part 25 in an up and down direction and a right and left direction, a treatment tool insertion part 222 through which a treatment tool such as living body forceps, a laser knife, or an inspection probe is inserted into the body cavity, and a plurality of switches 223 each of which is an operation input unit to input an operation instruction signal not only of the processing device 3 and the light source device 4 but also of a peripheral device such as an air conveyance unit, a water conveyance unit, or a gas conveyance unit. The treatment tool inserted from the treatment tool insertion part 222 passes through a treatment tool channel (not illustrated) of the distal end part 24 and comes out of an opening part (not illustrated).

The universal cord 23 at least includes a light guide 241 and a cable assembly 247 in which an optical fiber and a metal cable are assembled. The universal cord 23 includes a connector part 27 which can be attached to and detached from the light source device 4. A coil cable 27a having a coil shape is extended from the connector part 27 and a connector part 28 which can be attached to and detached from the processing device 3 is included at an extended end of the coil cable 27a. The connector part 27 includes an O/E converter 271, a field programmable gate array (FPGA) 272, an E/O converter 273, and a P/S converter 274.

The O/E converter 271 converts an optical signal corresponding to the image information transmitted from the distal end part 24 into an electric signal and outputs the converted signal to the FPGA 272.

The FPGA 272 outputs the electric signal, which is input from the O/E converter 271, to the processing device 3 through a transmission line selected by the selector 244k of the imaging element 244. More specifically, based on setting data transmitted from the selector 244k of the imaging element 244, when transmission of an optical signal is selected by the selector 244k, the FPGA 272 outputs, to the E/O converter 273, the image information input from the O/E converter 271. On the other hand, based on the setting data transmitted from the selector 244k of the imaging element 244, when transmission of an electric signal is selected by the selector 244k, the FPGA 272 outputs, to the P/S converter 274, the image information input from the O/E converter 271. Note that the P/S converter 274 may be embedded in the FPGA 272.

The E/O converter 273 converts an electric signal corresponding to the image information input from the FPGA 272 into an optical signal and outputs the converted signal to the processing device 3. In the present first embodiment, the E/O converter 273 functions as the second output unit.

The P/S converter 274 performs parallel/serial conversion of an electric signal corresponding to the image information input from the FPGA 272 and outputs the converted signal to the processing device 3. In the present first embodiment, the P/S converter 274 functions as the first output unit.

Then, a configuration of the processing device 3 will be described. The processing device 3 includes an O/E converter 300, an S/P converter 301, an image processing unit 302, a luminance detection unit 303, a dimmer unit 304, a read address setting unit 305, a driving signal generation unit 306, an input unit 307, a recording unit 308, a control unit 309, and a reference clock generation unit 310. Note that in the present first embodiment, a sequential lighting configuration will be described as an example of the processing device 3. However, application to a simultaneous lighting can be also performed.

The O/E converter 300 converts the optical signal input from the E/O converter 273 of the connector part 27 into an electric signal and outputs the converted signal to the image processing unit 302.

The S/P converter 301 perform serial/parallel conversion of image information (digital signal) of the electric signal input from the P/S converter 274 of the connector part 27 and outputs the converted information to the image processing unit 302.

Based on an electric signal of the image information input from the O/E converter 300 or the image information in a parallel form which information is input from the S/P converter 301, the image processing unit 302 generates an in-vivo image to be displayed by the display device 5. The image processing unit 302 includes a synchronizer 302a, a white balance (WB) adjustment unit 302b, a gain adjustment unit 302c, a γ correction unit 302d, a D/A converter 302e, a format changing unit 302f, a memory for a sample 302g, and a memory for a still image 302h.

The synchronizer 302a inputs image information, which is input as pixel information, into three memories (not illustrated) provided in each pixel. Then, the synchronizer 302a serially updates and holds a value in each memory while associating the value with an address of a pixel in the light receiving unit 244f which address is read by the reading unit 244g and synchronizes pieces of image information of these three memories as RGB image information. The synchronizer 302a serially outputs the synchronized RGB image information to the white balance adjustment unit 302b and outputs, to the memory for a sample 302g, a part of the RGB image information for image analysis such as luminance detection.

The white balance adjustment unit 302b performs a white balance adjustment of the RGB image information. More specifically, the white balance adjustment unit 302b performs adjustment in such a manner that an RGB image level of when a white chart to be a basis is captured becomes 1:1:1.

The gain adjustment unit 302c performs a gain adjustment of the RGB image information. The gain adjustment unit 302c outputs the gain-adjusted RGB signal to the γ correction unit 302d and outputs, to the memory for a still image 302h, a part of the RGB signal for a still-image display, an enlarged-image display, or an emphasized-image display.

The γ correction unit 302d performs a gradation correction (γ correction) of the RGB image information in accordance with the display device 5.

The D/A converter 302e converts, into an analog signal, the gradation-corrected RGB image information output from the γ correction unit 302d.

The format changing unit 302f changes the image information, which is converted into the analog signal, into a file format for a video which format is, for example, a hi-vision system. Then, the format changing unit 302f outputs the information to the display device 5.

The luminance detection unit 303 detects a luminance level corresponding to each pixel from the RGB image information held by the memory for a sample 302g. Then, the luminance detection unit 303 records the detected luminance level into a memory provided inside and outputs the luminance level to the control unit 309. Also, the luminance detection unit 303 calculates a gain adjustment value and a light emission quantity based on the detected luminance level. While outputting the gain adjustment value to the gain adjustment unit 302c, the luminance detection unit 303 outputs the light emission quantity to the dimmer unit 304.

Under control by the control unit 309, the dimmer unit 304 sets, for example, a light quantity or light emission timing which relates to illumination light generated by the light source device 4 based on the light emission quantity calculated by the luminance detection unit 303. Then, the dimmer unit 304 transmits the set light quantity or light emission timing to the light source device 4.

The read address setting unit 305 has a function to set order of reading pixels to be read on a light reception surface of the sensor unit 244a. That is, the read address setting unit 305 has a function to set an address of a pixel in the sensor unit 244a which address is read by the AFE part 244b. Also, the read address setting unit 305 outputs, to the synchronizer 302a, the set address information of the pixel to be read.

The driving signal generation unit 306 generates a timing signal for driving which signal is to drive the imaging element 244. Then, the driving signal generation unit 306 transmits the generated timing signal to the timing generator 244d through a predetermined signal line included in the cable assembly 247. The timing signal includes address information of the pixel to be read.

The input unit 307 receives an input of various signals such as an operation instruction signal to instruct an operation of the endoscope system 1.

The recording unit 308 is realized by a semiconductor memory such as a flash memory or a dynamic random access memory (DRAM). The recording unit 308 records various programs to operate the endoscope system 1 and data including various parameters necessary for the operation of the endoscope system 1. Also, the recording unit 308 includes an identification information recording unit 308a to record the identification information of the processing device 3. The identification information includes unique information (ID) of the processing device 3, a model year, spec information of the control unit 309, a transmission method, a transmission rate, and the like.

The control unit 309 includes a CPU or the like. The control unit 309 performs driving control of each configuration part including the distal end part 24 and the light source device 4 and performs input and output control of information with respect to each configuration part. The control unit 309 transmits setting data for imaging control to the imaging controller 244e through a predetermined signal line included in the cable assembly 247.

The reference clock generation unit 310 generates a reference clock signal to be a reference of an operation of each configuration part in the endoscope system 1 and supplies the generated reference clock signal to each configuration part in the endoscope system 1.

Then, a configuration of the light source device 4 will be described. The light source device 4 includes a light source 41, a light emitting diode (LED) driver 42, a rotary filter 43, a driving unit 44, a driving driver 45, and a light source controller 46.

The light source 41 includes a white LED and generates white light under control by the light source controller 46. The LED driver 42 generates white light in the light source 41 by supplying current to the light source 41 under control by the light source controller 46. The light generated by the light source 41 is emitted from a distal end of the distal end part 24 through the rotary filter 43, a condenser lens (not illustrated), and the light guide 241. Note that the light source 41 may include a xenon lamp or the like.

The rotary filter 43 is arranged on an optical path of the white light generated by the light source 41. By rotation of the rotary filter 43, only light, which has a predetermined wavelength band, in the white light generated by the light source 41 can be transmitted. More specifically, the rotary filter 43 includes a red filter 431, a green filter 432, and a blue filter 433 which respectively pass pieces of light having wavelength bands of red light (R), green light (G), and blue light (B). By the rotation of the rotary filter 43, pieces of light having wavelength bands of red, green, and blue (such as red: 600 nm to 700 nm, green: 500 nm to 600 nm, and blue: 400 nm to 500 nm) are serially transmitted. Accordingly, any one of narrow-banded red light, green light, and blue light derived from the white light generated by the light source 41 can be serially emitted to the endoscope 2.

The driving unit 44 includes, for example a stepping motor or a DC motor and makes the rotary filter 43 rotated. Under control by the light source controller 46, the driving driver 45 supplies predetermined current to the driving unit 44.

The light source controller 46 controls an amount of current supplied to the light source 41 according to a light source synchronization signal transmitted from the dimmer unit 304. Also, the light source controller 46 rotates the rotary filter 43 by driving the driving unit 44 through the driving driver 45 under control by the control unit 309.

The display device 5 has a function to receive the in-vivo image generated by the processing device 3 from the processing device 3 through a video cable and to display the in-vivo image. The display device 5 includes a liquid-crystal or organic electro luminescence (EL).

Figure 3:
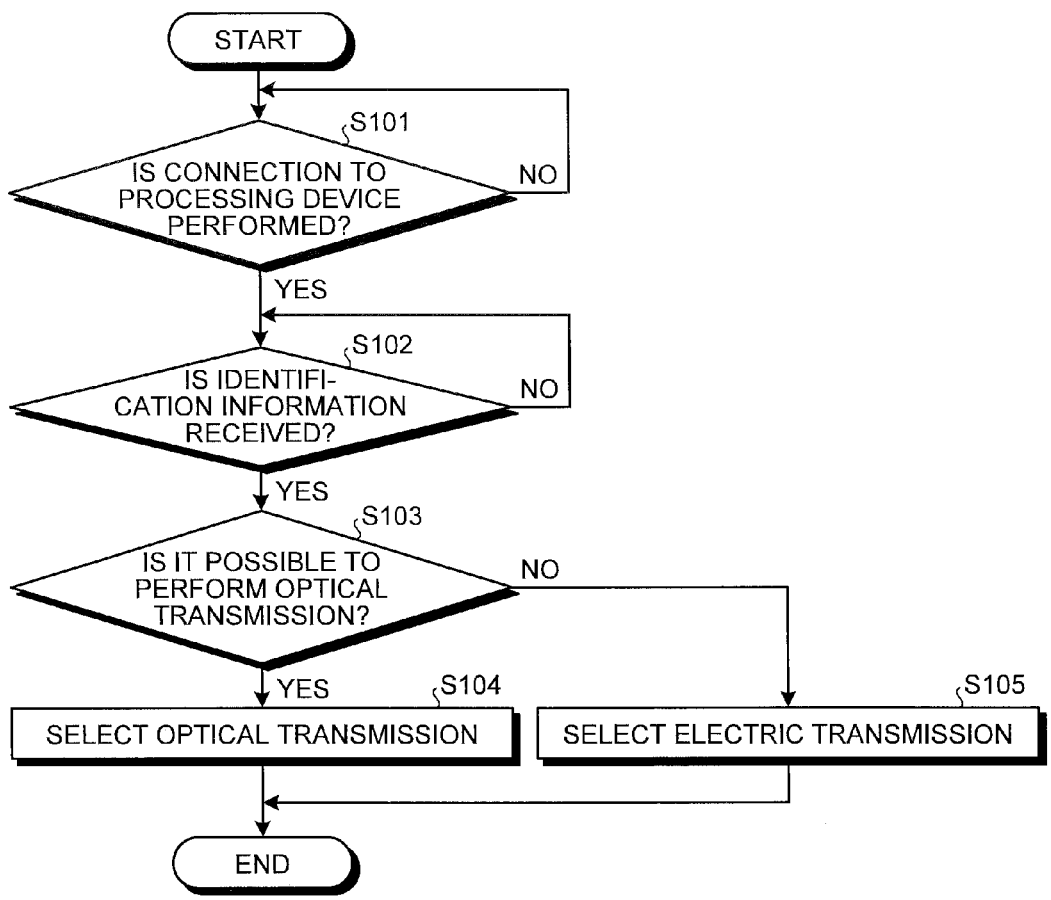
FIG. 3 is a flowchart illustrating an outline of switching processing of a transmission line which processing is executed by the endoscope system according to the first embodiment of the present invention.

Switching processing to switch a transmission line of image information which processing is executed by the endoscope system 1 including the above configuration will be described. FIG. 3 is a flowchart illustrating an outline of the switching processing of a transmission line which processing is executed by the endoscope 2 of the endoscope system 1 according to the present first embodiment. Note that the following switching processing is performed during an initial operation after the power is turned on in the endoscope system 1, is performed before a practitioner starts an inspection of a subject by using the endoscope system 1, or is performed at each predetermined timing during the inspection of the subject.

As illustrated in FIG. 3, the imaging controller 244e determines whether the connector part 27 of the endoscope 2 is connected to the processing device 3 (step S101). When the imaging controller 244e determines that the connector part 27 of the endoscope 2 is connected to the processing device 3 (step S101: Yes), the endoscope system 1 transitions to step S102. On the other hand, when the imaging controller 244e determines that the connector part 27 of the endoscope 2 is not connected to the processing device 3 (step S101: No), the endoscope system 1 repeatedly performs the determination.

Subsequently, the imaging controller 244e determines whether identification information included in setting data is received from the processing device 3 (step S102). When the imaging controller 244e determines that the identification information is received (step S102: Yes), the endoscope system 1 transitions to step S103. On the other hand, when the imaging controller 244e determines that identification information is not received (step S102: No), the endoscope system 1 keeps performing the determination.

Then, based on the identification information, the selector 244k determines whether the processing device 3 can perform reception by optical transmission (step S103). When the processing device 3 can perform reception by the optical transmission (step S103: Yes), the selector 244k selects optical transmission as a transmission line of the image information output from the FPGA 272 (step S104). More specifically, the selector 244k selects the E/O converter 273 as a destination of an output of the image information which output is performed by the FPGA 272. Accordingly, image information (image data) captured by the imaging element 244 is output as an optical signal to the processing device 3 through the optical fiber included in the cable assembly 247. As a result, the endoscope 2 can transmit a large amount of image information to the processing device 3 in one transmission without mixture of a disturbance noise from an electric knife or the like. Then, the endoscope system 1 ends the present processing.

On the other hand, when the processing device 3 cannot perform reception by the optical transmission (step S103: No), the selector 244k selects electric transmission as transmission of the image information output from the FPGA 272 (step S105). More specifically, the selector 244k selects the P/S converter 274 as a destination of an output of the image information which output is performed by the FPGA 272. Accordingly, the image information captured by the imaging element 244 is output as an electric signal to the processing device 3. As a result, the endoscope 2 can transmit image information as an electric signal even to the processing device 3 which can only receive an electric signal. Then, the endoscope system 1 ends the present processing.

According to the above-described first embodiment of the present invention, the selector 244k selects one of optical transmission and electric transmission as transmission of image information based on the identification information included in the setting data transmitted from the processing device 3. Accordingly, image information can be transmitted regardless of performance of the processing device 3 to which the endoscope 2 is connected. As a result, according to the present first embodiment, aggravation of electromagnetic interference and mixture of a disturbance noise due to high-speed communication can be prevented in the processing device 3 which can receive image information by the optical transmission. Also, compatibility with the processing device 3 which can receive image information by the electric transmission can be included.

Figure 4:
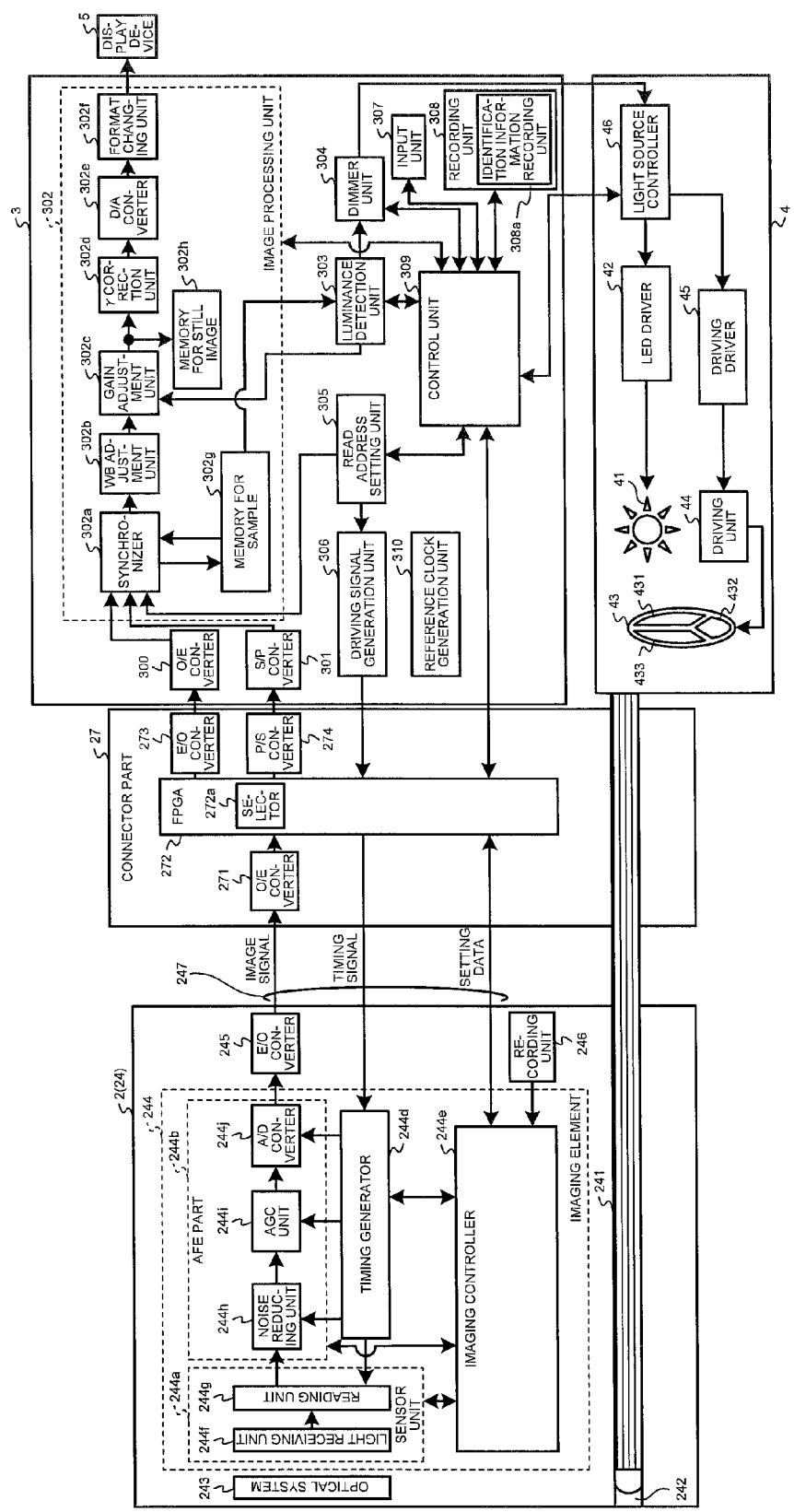
FIG. 4 is a block diagram illustrating a functional configuration of a main part of an endoscope system according to a modification example of the first embodiment of the present invention.

Note that in the present first embodiment, the imaging controller 244e includes the selector 244k. However, for example, as illustrated in FIG. 4, a selector 272a may be provided in the FPGA 272 of the connector part 27. Accordingly, the imaging element 244 and the distal end part 24 can be further downsized. In this case, wireless communication may be performed by setting the E/O converter 273 as a light emission unit to emit light according to an electric signal and by replacing the O/E converter 300 with a receiving unit to receive the light. Accordingly, a diameter of the connector part 27 can be reduced. Also, the E/O converter 273 and a light emission unit may be separately provided in the connector part 27.

Also, in the present first embodiment, the selector 244k selects a destination of an output of the image information based on the identification information of the processing device 3. However, for example, the control unit 309 of the processing device 3 may output a discrimination signal indicating that transmission as an optical signal can be performed and a destination of an output of the image information may be selected based on the discrimination signal.

Also, in the present first embodiment, based on the number of bits of serial data of the setting data transmitted from the processing device 3 or discrimination information (flag indicating that optical transmission can be performed) added to a bit, the selector 244k may select a destination of an output of the image information.

Also, in the present first embodiment, when the selector 244k selects the P/S converter 274 as a destination of an output of the image information, the FPGA 272 may perform compression processing or reduction processing of the image information and may perform an output to the processing device 3. For example, the FPGA 272 may perform the reduction processing or the like of a data amount of the image information by reducing resolution or gradation. Also, the FPGA 272 may smooth image information to be output in a unit time and may perform an output to the processing device 3. Also, when an observation method of the endoscope system 1 is a simultaneous lighting, the FPGA 272 may output the image information in order of RGB to the processing device 3.

Also, in the present first embodiment, only image information is transmitted as an optical signal. However, for example, a converter to convert a different electric signal such as setting data and a timing signal into an optical signal and a wavelength multiplex unit to multiplex the optical signal, which is converted by the converter, with a wavelength of the optical signal of image information may be provided and transmission and reception may be performed through one transmission line (optical fiber).

Also, in the present first embodiment, the recording unit 246 is provided in the distal end part 24. However, the recording unit 246 may be provided in the connector part 27. Accordingly, the distal end part 24 can be downsized.

Second Embodiment

Next, the second embodiment of the present invention will be described. In an endoscope system according to the present second embodiment, configurations of the endoscope and the processing device in the endoscope system according to the above-described embodiment are different. More specifically, an endoscope includes a recording unit and a control unit of a processing device includes a selector. Thus, in the following, after a processing device of an endoscope system according to the present second embodiment is described, processing executed by the endoscope system according to the present second embodiment will be described. Note that the same reference signs are used to designate the same configurations.

Figure 5:
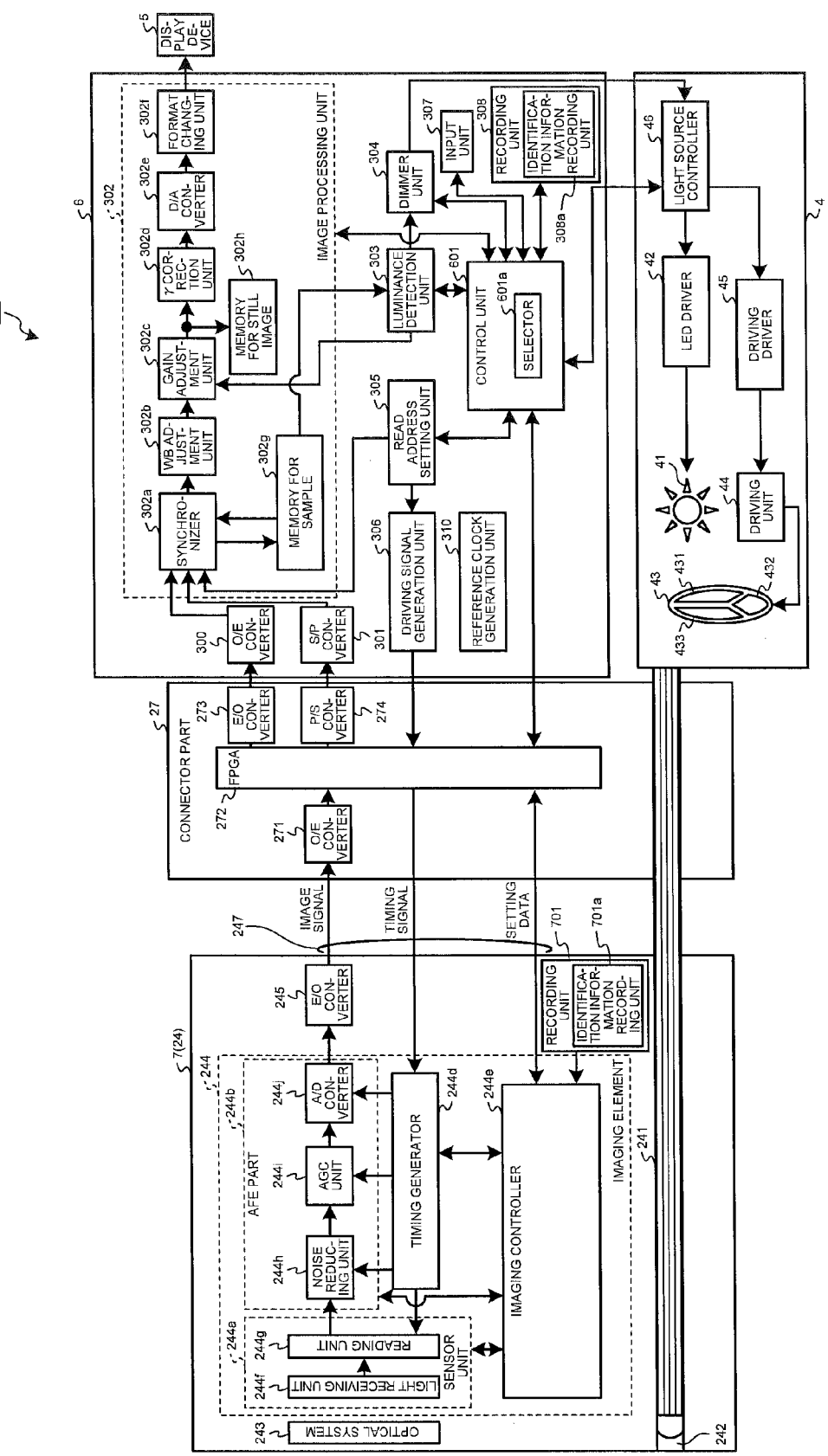
FIG. 5 is a block diagram illustrating a functional configuration of a main part of an endoscope system according to a second embodiment of the present invention.

FIG. 5 is a block diagram illustrating a functional configuration of a main part of an endoscope system 100 according to the present second embodiment. As illustrated in FIG. 5, the endoscope system 100 includes an endoscope 7 and a processing device 6. A distal end part 24 of the endoscope 7 includes a recording unit 701.

The recording unit 701 records various kinds of information of the endoscope 7. More specifically, the recording unit 701 records various programs to operate an imaging element 244 and data including various parameters necessary for the operation of the imaging element 244. Also, the recording unit 701 includes an identification information recording unit 701a to record identification information to identify the endoscope 7. Here, the identification information includes unique information (ID) of the endoscope 7, a model year, spec information of the imaging element 244, a transmission method, a transmission rate, and the like.

The processing device 6 includes a control unit 601. The control unit 601 includes a CPU or the like and performs driving control of each configuration part including the distal end part 24 and a light source device 4 and input and output control of information with respect to each configuration part. The control unit 601 transmits setting data for imaging control to an imaging controller 244e through a predetermined signal line included in a cable assembly 247. Also, the control unit 601 includes a selector 601a.

When the endoscope 2 is connected to the processing device 6, the selector 601a selects, based on the identification information received from the endoscope 2, one of a first receiving unit and a second receiving unit as a receiving unit to receive image information generated by the imaging element 244. For example, based on setting data received from the endoscope 7, the selector 601a selects a transmission line of the image information generated by the imaging element 244. More specifically, based on the identification information received from the endoscope 7, the selector 601a selects a transmission method of image information by selecting one of an O/E converter 300 and an S/P converter 301 as a receiving unit to receive image information.

Figure 6:
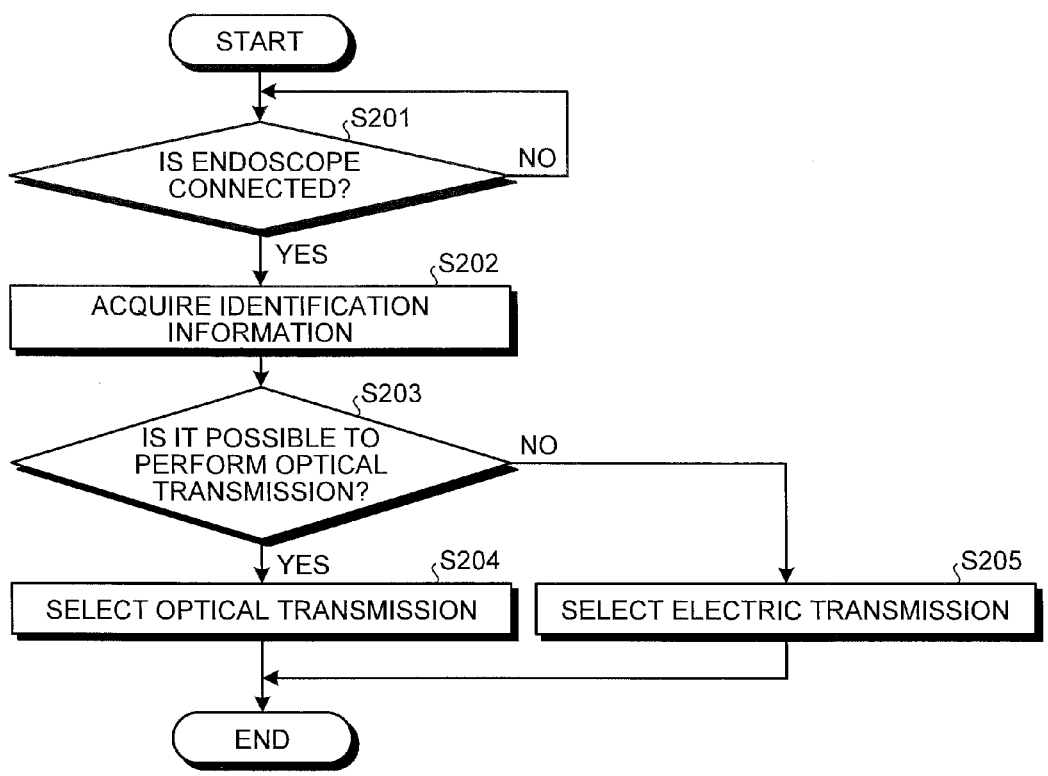
FIG. 6 is a flowchart illustrating an outline of switching processing of a transmission line which processing is executed by the endoscope system according to the second embodiment of the present invention.

Switching processing to switch a transmission line of image information which processing is executed by the endoscope system 100 including the above configuration will be described. FIG. 6 is a flowchart illustrating an outline of the switching processing of a transmission line which processing is executed by the endoscope system 100 according to the present second embodiment. Note that the following switching processing is performed during an initial operation after the power is turned on in the endoscope system 100, is performed before a practitioner starts an inspection of a subject by using the endoscope system 100, or is performed at each predetermined timing during the inspection of the subject.

As illustrated in FIG. 6, the control unit 601 determines whether a connector part 27 of the endoscope 7 is connected to the processing device 6 (step S201). When the control unit 601 determines that the connector part 27 of the endoscope 7 is connected to the processing device 6 (step S201: Yes), the endoscope system 100 transitions to step S202. On the other hand, when the control unit 601 determines that the connector part 27 of the endoscope 7 is not connected to the processing device 6 (step S201: No), the endoscope system 100 repeatedly performs the determination.

Then, the control unit 601 acquires identification information to identify the endoscope 7 from the identification information recording unit 701a of the endoscope 7 (step S202).

Then, based on the acquired identification information, the selector 601a determines whether the endoscope 7 can perform transmission by optical transmission (step S203). When the endoscope 7 can perform transmission by the optical transmission (step S203: Yes), the selector 601a selects the optical transmission as a transmission line of image information output from an FPGA 272 (step S204). More specifically, the selector 601a selects the O/E converter 300 as a destination of reception of the image information output from the FPGA 272. Accordingly, image information captured by the imaging element 244 is transmitted as an optical signal to the processing device 6. As a result, the processing device 6 can receive a large amount of image information without mixture of a disturbance noise from an electric knife or the like. Then, the endoscope system 100 ends the present processing.

On the other hand, when the endoscope 7 cannot perform transmission by the optical transmission (step S203: No), the selector 601a selects electric transmission as a transmission line of the image information output from the FPGA 272 (step S205). More specifically, the selector 601a selects the S/P converter 301 of the processing device 6 as a destination of an output of the image information which output is performed by the FPGA 272. Accordingly, the image information captured by the imaging element 244 is transmitted as an electric signal to the processing device 6. As a result, the processing device 6 can receive image information even from the endoscope 7 which can only transmit an electric signal. Then, the endoscope system 100 ends the present processing.

According to the above-described second embodiment of the present invention, the selector 601a selects one of optical transmission and electric transmission as transmission of image information based on identification information included in setting data transmitted from the endoscope 7. Accordingly, image information can be received regardless of performance of the endoscope 7 to which the processing device 6 is connected. As a result, according to the present second embodiment, in an endoscope which can transmit image information by optical transmission, aggravation of electromagnetic interference and mixture of a disturbance noise due to high-speed communication can be prevented. Also, compatibility with an endoscope which can transmit image information by electric transmission can be included.

According to some embodiments, it is possible to select one of optical transmission and electric transmission as transmission unit of image information based on identification information to which a selector is connected. Accordingly, it is possible to switch a transmission method according to a connection object. Thus, it is possible to transmit or receive image information regardless of performance of a connection destination. As a result, in a processing device which can receive image information by optical transmission, aggravation of electromagnetic interference and mixture of a disturbance noise due to high-speed communication can be prevented. Also, compatibility with a processing device which can receive image information by electric transmission can be included.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope which is configured to be connected to an external processing device and to transmit and receive information to and from the processing device, the endoscope comprising:
    an insertion part configured to be inserted into a body cavity of a subject;
    a distal end part provided at a distal end of the insertion part, the distal end part including:
        an imaging unit configured to generate image information; and
        an E/O converter configured to convert the image information generated by the imaging unit into an optical signal and to output the converted optical signal;
    a connector part connected to the processing device, the connector part including:
        an O/E converter configured to convert the optical signal output from the E/O converter into an electric signal;
        a first output unit configured to convert the electric signal converted by the O/E converter into serial data and to output the converted serial data to the processing device;
        a second output unit configured to convert the electric signal converted by the O/E converter into an optical signal and to output the converted optical signal to the processing device; and
        a selector configured to select, based on identification information of the processing device, one of the first output unit and the second output unit as an output unit to output the image information; and
    an optical fiber connecting the E/O converter to the O/E converter.

* * * * *